(12) United States Patent
Timothy

(10) Patent No.: US 8,481,804 B2
(45) Date of Patent: Jul. 9, 2013

(54) WOUNDDRESSING AND HEADGEAR

(76) Inventor: Jake Timothy, Leeds (GB)

( * ) Notice: Subject to any disclaimer, the term of this patent is extended or adjusted under 35 U.S.C. 154(b) by 145 days.

(21) Appl. No.: 12/999,181

(22) PCT Filed: Jun. 17, 2009

(86) PCT No.: PCT/GB2009/050688
§ 371 (c)(1),
(2), (4) Date: Mar. 2, 2011

(87) PCT Pub. No.: WO2009/153594
PCT Pub. Date: Dec. 23, 2009

(65) Prior Publication Data
US 2011/0144555 A1    Jun. 16, 2011

(30) Foreign Application Priority Data
Jun. 18, 2008   (GB) .................................. 0811136.1

(51) Int. Cl.
*A61F 13/00*    (2006.01)
*A61K 9/70*    (2006.01)
*A61B 17/00*    (2006.01)

(52) U.S. Cl.
USPC ............. 602/53; 606/201; 424/449; 604/304

(58) Field of Classification Search
USPC ............... 602/41–42, 60–68, 1, 5, 17, 53; 604/304–308, 77–79; 424/443, 445, 446, 424/447, 449; 606/201
See application file for complete search history.

(56) References Cited

U.S. PATENT DOCUMENTS

| | | | | |
|---|---|---|---|---|
| 5,014,365 A | * | 5/1991 | Schulz | 2/412 |
| 5,267,365 A | * | 12/1993 | Walter | 5/683 |
| 5,752,298 A | * | 5/1998 | Howell | 24/593.1 |
| 6,656,143 B2 | * | 12/2003 | Browd | 602/13 |
| 2003/0212357 A1 | | 11/2003 | Pace | |
| 2006/0174895 A1 | * | 8/2006 | Ferguson et al. | 128/845 |
| 2009/0177134 A1 | * | 7/2009 | Timothy | 602/53 |

FOREIGN PATENT DOCUMENTS

| | | |
|---|---|---|
| GB | 2435833 A | 9/2007 |
| JP | H08300464 | 11/1996 |
| JP | 2006501941 A | 1/2006 |
| WO | WO-2005/097022 A1 | 10/2005 |
| WO | WO-2007/101990 A1 | 9/2007 |

OTHER PUBLICATIONS

Westberg, Erika, "International Search Report", for PCT/GB2009/050688 as mailed Oct. 21, 2009, 5 pages.

* cited by examiner

*Primary Examiner* — Patricia Bianco
*Assistant Examiner* — Tarla Patel
(74) *Attorney, Agent, or Firm* — Winstead PC

(57) ABSTRACT

A wound dressing comprising a sealed enclosure having at least one compartment; a plurality of spaced apart pillar-like structures positioned within the at least one compartment; and means for evacuating air from the at least one compartment, wherein the evacuation of air from the at least one compartment causes a reduction in the distance between at least two of the pillar-like structures.

22 Claims, 5 Drawing Sheets

WOUNDDRESSING AND HEADGEAR

BACKGROUND OF THE INVENTION

1. Technical Field

The present invention relates to a wound dressing, in particular, to an improved wound dressing for reducing post-operative swelling of a body part of a human or animal patient, or for controlling blood loss from wounds.

The invention also relates to a method for reducing post-operative swelling of a body member of a human or animal patient, or for controlling blood loss from wounds.

2. History of Related Art

Post-operative swelling results from the accumulation of bodily fluid around an operation wound. Post-operative swelling cannot be eliminated altogether because following an operation the wound needs a blood supply to enable healing which inevitably results in some leakage and, hence, swelling.

Since swelling can hinder recovery and in some cases lead to further complications, it is always an issue that is sought to be minimised.

The control of blood loss, especially following a serious accident, is of great importance as excessive loss of blood can hamper recovery leading to medical complications or even fatality.

The use of bandages is known in the art in order to minimise post-operative swelling or to control blood loss. The use of bandages is appealing since they are generally versatile in that they can be readily adapted for use on different body members and on wounds of different sizes.

However when used as an aid for minimising post-operative swelling, bandages can be bulky and cumbersome. This is especially the case in relation to head injuries where most of the bandage employed does not come into contact with the wound but rather is around the head merely holding a small part of the bandage against the wound. Moreover, wounds need to be checked periodically, to ensure that there is not excessive leakage of fluid from the wound. Generally, bandages are disposed of when a wound is checked and this is wasteful.

There are a number of devices known in the art directed at minimising post-operative swelling in patients undergoing surgery on the head.

WO2005/097022 discloses a post-operative head dressing comprising a rigid cap adapted to fit over the head of a patient, and a liner. The liner is a network of tubes of resilient material connected to a single opening through which gas may be introduced to pressurise the liner network. The liner expands against the cap to squeeze the head.

GB 2435833 discloses a post-operative head dressing comprising a cap adapted to fit over the head of a patient. The cap is a patchwork of compartments of airtight flexible material which are evacuated during use, whereby atmospheric pressure compresses the flexible material. The compartments are filled with beads, preferably polystyrene beads, so that, on air evacuation, the cap not only becomes rigid, but also gently pressed against the scalp to inhibit post-operative swelling and/or bleeding from head wounds.

SUMMARY OF THE INVENTION

According to a first aspect of the invention there is provided a wound dressing comprising a sealed enclosure having at least one compartment; a plurality of spaced apart pillar-like structures (hereinafter "pillars") positioned within the at least one compartment; and means for evacuating air from the at least one compartment, wherein the evacuation of air from the at least one compartment causes a reduction in the distance between at least two of the pillars.

The reduction in the distance between at least two of the pillars has the effect of reducing the overall length of the bandage resulting in the exertion of pressure by the dressing to the wound in use thus restricting the amount of swelling that may occur. The present invention thus provides an improved wound dressing that stems swelling and bleeding of a wound.

The pillars may be formed from any suitable material. Ideally the pillars are formed from either a rubber based material, a silicon based material or an elastomeric polymer.

Preferably the pillars are spaced apart from each other in a predetermined arrangement.

By arranging the pillars in a predetermined arrangement, the way in which pressure can be exerted onto a body member when air is evacuated from the compartment can be controlled. For example, arrangement of the pillars in long thin parallel strips will result in greater reduction along one axis than another.

Conveniently the pillars are evenly spaced within the compartment. By having the pillars evenly spaced from each other, an equal reduction in the distance between adjoining pillars will take place, hence resulting in the application of uniform pressure across a body part once air has been evacuated from the compartment.

Preferably the pillars are cylindrical columns, however, the pillars may be formed of columns having any suitable cross-sectional geometry. For example, the pillars could be triangular, rectangular, hexagonal etc in cross-section.

Advantageously each pillar is connected to a neighbouring pillar by a connecting member in order to define a lattice-like structure.

Connecting the pillars to a neighbouring structure removes the need for re-adjusting the positions of the structures relative to each other after use, as is generally required in the prior art dressings mentioned above that incorporate bead structures.

The connecting members may be integrally formed with the pillars. Alternatively the connecting members may be bonded with the pillars.

Preferably the sealed enclosure comprises a first and second film layer.

The first and second film layers may be formed of any suitable material. Ideally the first and second film layers are formed from a vacuum formable material such as PVC.

Preferably the first and second film layers are bonded together around their edges to define the sealed enclosure. The pillars are thus retained between the first and second film layers.

The first and second film layers may be bonded together by any suitable means, for example the film layers may be heat sealed, ultrasonically welded or glued together.

Preferably the plurality of pillars are moveably retained between the first and second film layers.

Preferably the plurality of pillars are retained in position between the first and second film layers by connection to the first and/or second film layer.

The pillars may be retained in position between the first and second film layers by any suitable means, for example by a heat seal, an ultrasonic weld or glue.

Preferably the plurality of pillars are integrally formed with at least one of the film layers.

Preferably a portion of the first film layer is adapted to be drawn into the space between the at least two pillars when air is evacuated from the compartment. As the first film layer is drawn into the space the dimensions of the wound dressing are reduced, causing a reduction in the distance between the at least two pillars.

Preferably the wound dressing further comprises a frame portion for attaching the dressing to a head of a patient.

Conveniently the frame portion comprises a securing band for securing the dressing onto the head of a patient.

Preferably the frame portion comprises means for adjusting the working length of the securing band.

The means for adjusting the working length of the securing band allows the wound dressing to be used with different size heads.

Preferably the means for adjusting the working length of the securing band comprises a pawl and ratchet mechanism.

The pawl and ratchet mechanism may be a self limiting pawl and ratchet mechanism of the type known in the art.

Preferably the means for adjusting the size of the securing band comprises a clip adjuster.

Preferably the frame portion further comprises a retaining member which is adapted, in use, to restrict the removal of the wound dressing independently of the securing band.

Preferably the frame portion comprises a flexible plastic material.

The flexible plastic material is preferably a thermoplastic material, ideally an acrylonitrile butadiene styrene (ABS) or a polypropene (PB).

Preferably the means for evacuating air from the at least one compartment comprises a vacuum release valve.

The means for evacuating air from the at least one compartment may further comprise a non-return valve in order to prevent the regression of air into the at least one compartment during the evacuation of air from the compartment.

Preferably the wound dressing further comprises means for introducing air into the at least one compartment. The means for introducing air into the at least one compartment may be in the form of a hand pump or an inlet valve connectable to a compressor.

According to a second aspect of the invention there is provided a method of reducing post-operative swelling of a body member of a human or animal patient, or for controlling blood loss from wounds comprising the steps of:
 a) applying to the body member or wound a dressing formed by a sealed enclosure having at least one compartment and a plurality of spaced apart pillars; and
 b) applying pressure onto the body member or wound by reducing the spacing between at least one pair of pillars by evacuating the at least one compartment of air.

According to a third aspect of the invention there is provided a headgear comprising a head covering portion and a frame portion comprising a securing band, wherein the frame portion further comprises at least one retaining member positioned on a side of the headgear which, in use, restricts the removal of the headgear independently of the securing band.

The third aspect of the invention thus enables a headgear to be secured on the head of a user without the need of a chin strap as securement of the headgear will be provided by the securing band and the at least on retaining member.

BRIEF DESCRIPTION OF THE DRAWINGS

There now follows a description of preferred embodiments of the invention, by way of non-limiting example, with reference being made to the accompanying drawings, in which.

DETAILED DESCRIPTION OF THE DRAWINGS

Figure 1:
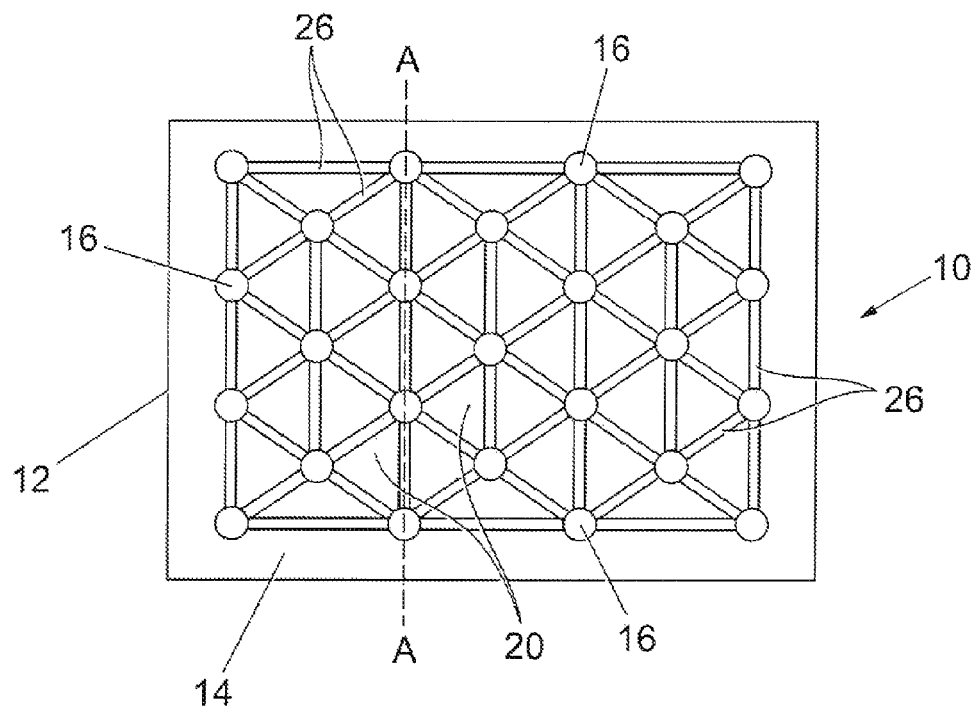
FIG. 1 is a plan view of a first embodiment of a wound dressing according to the invention.
Figure 2:
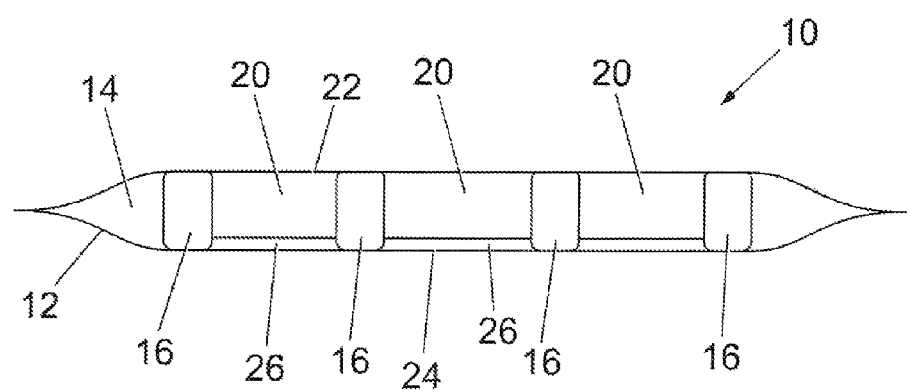
FIG. 2 is a cross-sectional view of the wound dressing of FIG. 1 taken along line A-A in FIG. 1.

Referring to FIGS. 1 and 2, a first embodiment of a wound dressing (10) according to the invention is shown. The wound dressing (10) comprises a sealed enclosure (12) having at least one compartment (14); a plurality of spaced apart pillars (16) positioned within the at least one compartment (14); and means for evacuating air from the at least one compartment (not shown).

The sealed enclosure (12) comprises a first film layer (22) and a second film layer (24) which are sealed together around their edges to define the sealed enclosure (12). The first and second film layers (22, 24) may additionally be bonded together at various points in order to define one or more further compartments within the sealed enclosure (12).

The first and second film layers (22, 24) are made of PVC material and are heat sealed to one another to define the sealed enclosure (12) and/or compartments.

The pillars (16) are substantially cylindrical in shape and are connected to a neighbouring structure by means of a connecting member (26). In this arrangement the pillars (16) and the connecting members (26) define a lattice-like structure. In a preferred embodiment, the pillars are made from a silicon based material and the connecting members (26) are made of a resilient material such as a flexible plastic material.

The pillars (16) may be moveably retained between the first and second film layers (22, 24) or may be retained in position between the film layers (22, 24) by connection to the first and/or second film layer.

The means for evacuating air from the at least one compartment is in the form of a vacuum release valve (not shown) having a non-return valve in order to prevent regression of air into the at least one compartment during evacuation of air from the compartment (14).

Figure 3A:
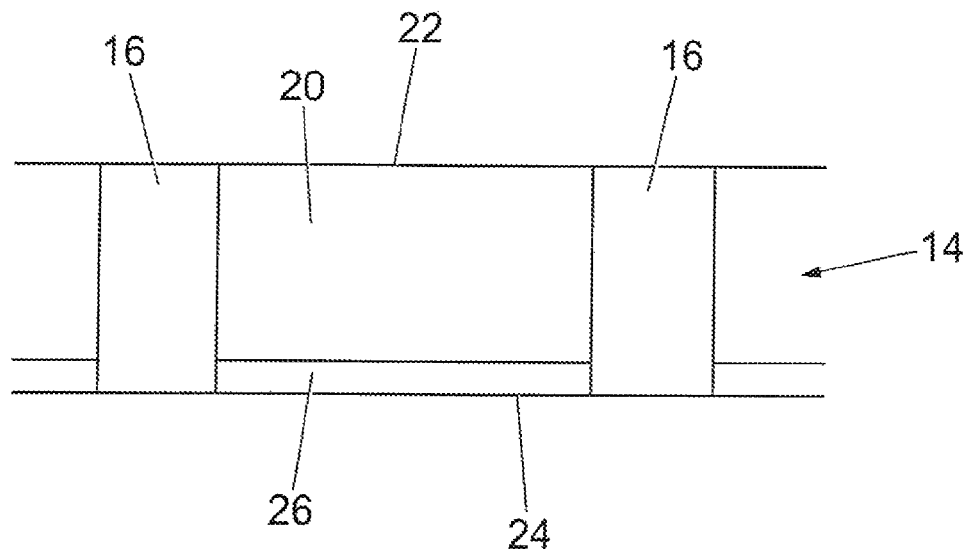
FIG. 3a is a schematic view of a section of the wound dressing of FIG. 1 showing the spacing between two pillars prior to evacuation of air from the compartment.
Figure 3B:
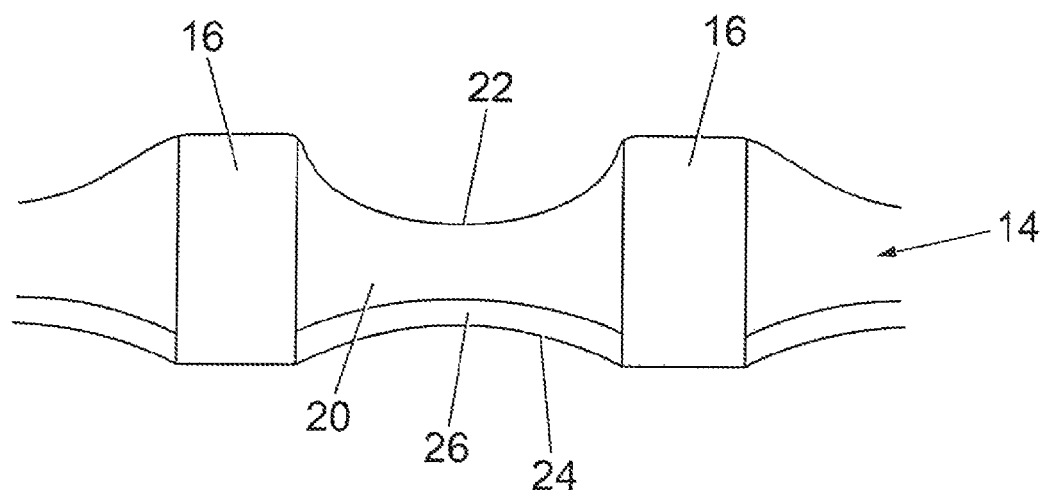
FIG. 3b is a schematic view of the section shown in FIG. 3a following the evacuation of air from compartment.

Referring to FIGS. 3a and 3b, when air is evacuated from the compartment (14), a portion of the first film layer (22) and a portion of the second film layer (24) are pulled into the space (20) between two adjoining pillars (16) (as best seen in FIG. 3b). As the film layers (22, 24) are pulled into the space (20) by the vacuum left by the evacuation of air therefrom, the overall surface area of the wound dressing (10) is reduced causing a reduction in the spacing between the adjoining pillars (16).

As the adjoining pillars (16) are drawn towards one another, the connecting members (26) are caused to flex inwardly into the space (20).

The film layers (22, 24) provide a controlled and self-limiting decrease in length of the wound dressing (10) in one or two axis as air is expelled.

When air is reintroduced into the compartment (14), the pillars (16) are returned to their original spacing due to the resiliency of the connecting members (26) causing the connecting members (26) to straighten and hence push the pillars (16) away from each other.

The pillars (16) are spaced apart from each other in a predetermined arrangement depending on requirements. That is to say the shape and spacing of the lattice elements (i.e. the pillars (16) and connecting members (26)) will determine how the wound dressing (10) changes when a vacuum is applied. For example, if the pillars (16) are arranged in a series of long thin strips that are parallel to one another there will be a greater reduction along the transverse axis than the longitudinal axis.

The wound dressing (10) further comprises means for introducing air into the at least one compartment (not shown) which may be in the form of a hand pump or an inlet valve connectable to a compressor.

Figure 4:
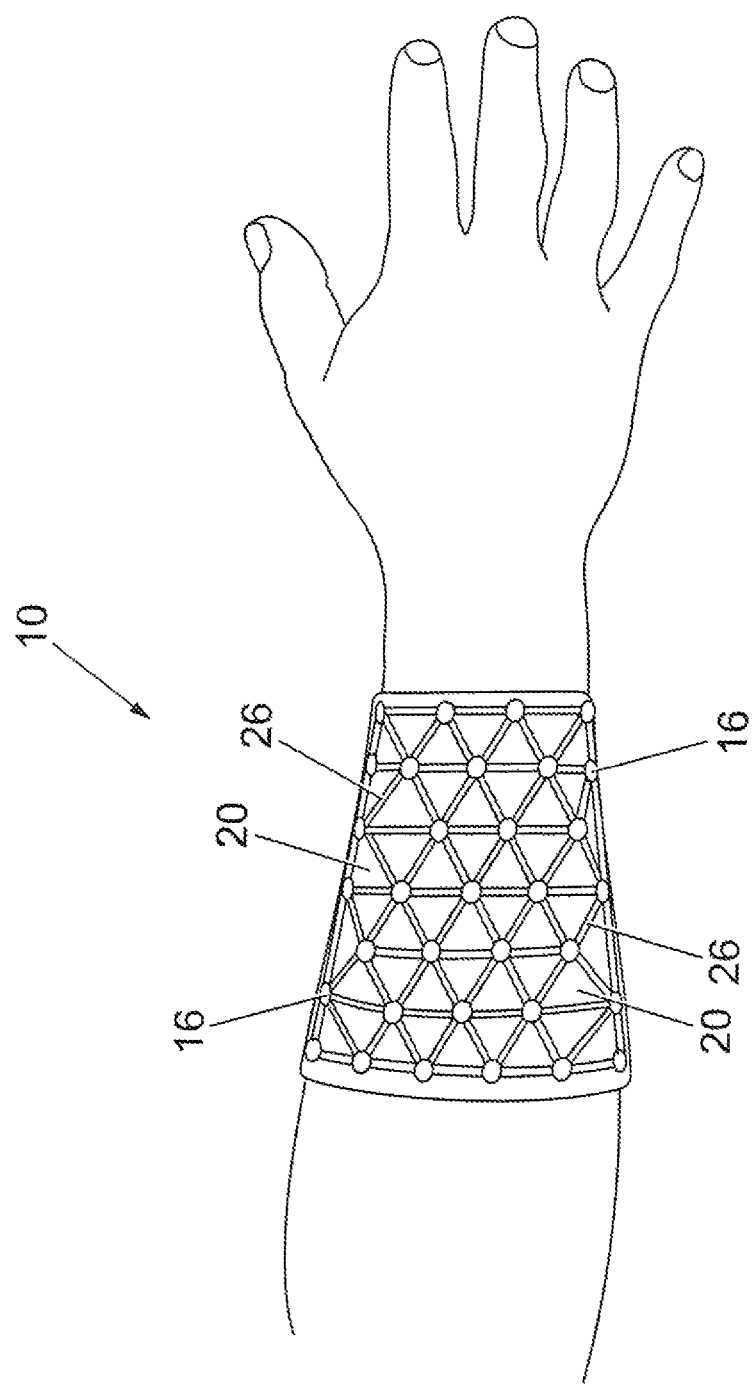
FIG. 4 is a schematic view showing the application of a wound dressing according to the invention applied to an arm of a patient.

Referring to FIG. 4, a wound dressing according to a first embodiment of the invention is shown applied to an arm of a patient in order to reduce post-operative swelling of the arm of a patient.

The wound dressing is first positioned around the post-operative wound and secured in place by a suitable means such as a band, a strap, a fastener sold under the trademark VELCRO®, tape or the like. Pressure is then applied onto the body member to constrict swelling of the body member by evacuating the at least one compartment of air. As described above, evacuation of air results in the film layers (22, 24) being pulled down into the space (20) between the pillars (16) results in the pulling of the pillars (16) closer together and a reduction of the overall dimensions of the wound dressing (10).

Figure 5:
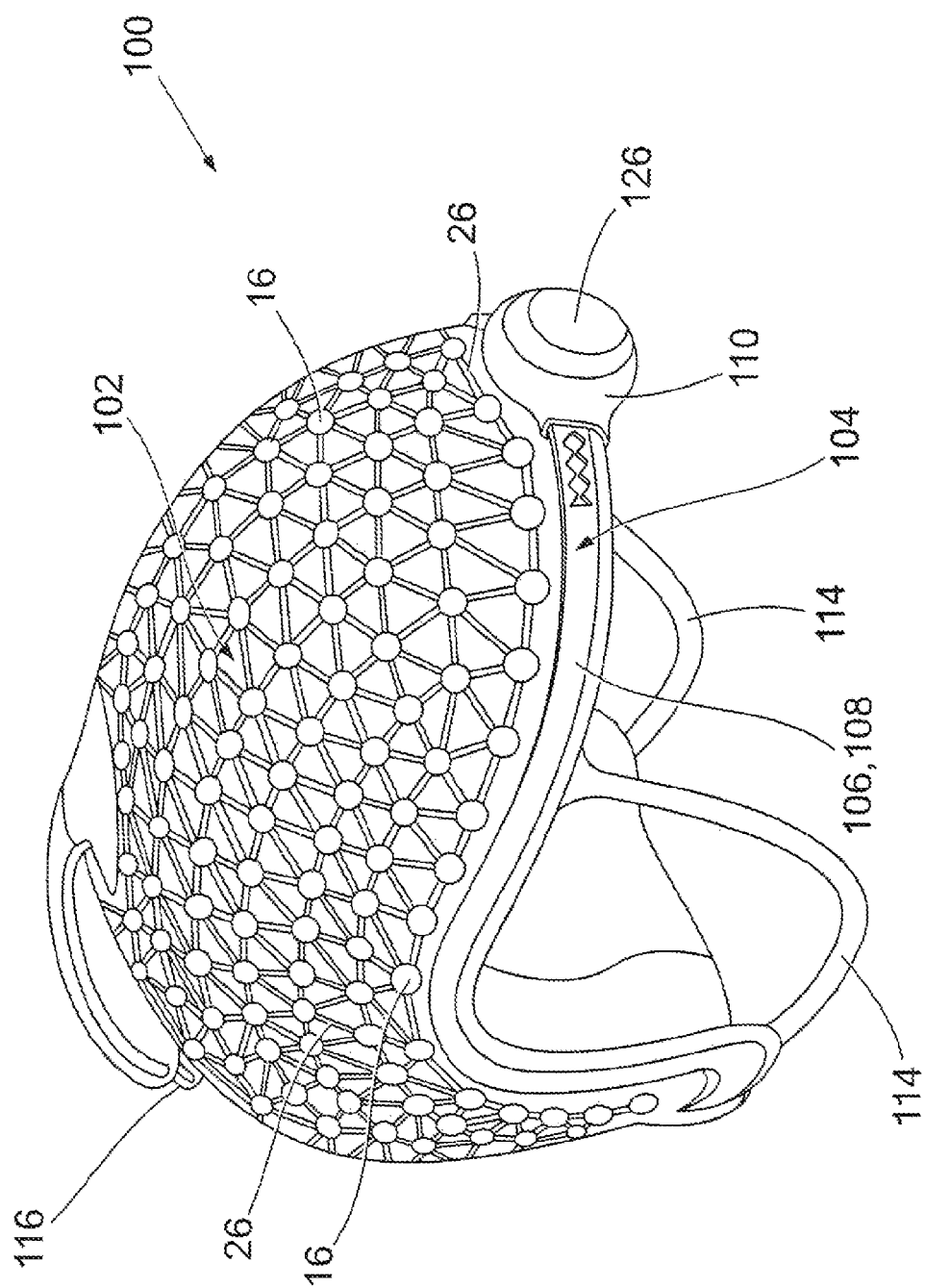
FIG. 5 is a perspective view of a second embodiment of a wound dressing according to the invention in the form of a head wound dressing.

Referring to FIG. 5, a second embodiment of a wound dressing according to the invention is shown. The wound dressing (100) is in the form of a head wound dressing and comprises a head covering portion (102) and a frame portion (104) for attaching the dressing to a head of a patient.

The head covering portion (102) is a similar construction to the wound dressing (10) described above and the same reference numerals have been used to identify identical features.

The frame portion (104) comprises a securing band (106) for securing the dressing (100) to the head of a patient and a pair of restraining members (114) positioned on opposite sides of the dressing (100) and located so as to be positioned on either side of a patient's head when worn.

The components of the frame portion (104) are produced from a flexible plastic in order to allow them to conform comfortably around the head whilst being rigid enough not to stretch and allow the wound dressing (100) to be able to be unwilling pulled off the head.

The securing band (106) is adapted to run circumferentially around the head of a patient. In the embodiment shown, the securing band (106) comprises two band members (108) each adapted to run from the forehead of user, along the temple and down such that it finishes below the occipital lobe to provide a secure hold.

The frame portion (104) further comprises means for adjusting the active length of the securing band (106). In the embodiment shown, the dressing (100) comprises a first means for adjusting the active length of the securing band (106) located at the front of the wound dressing (100) and a second means for adjusting the active length of the securing band (106) located at the rear of the wound dressing (100).

The front adjusting means is a pawl and ratchet mechanism (110) coupled to a first end of the two band members (108). The pawl and ratchet mechanism includes a knob (126) for adjusting the tension of a frontal section of the securing band (106).

Figure 6:
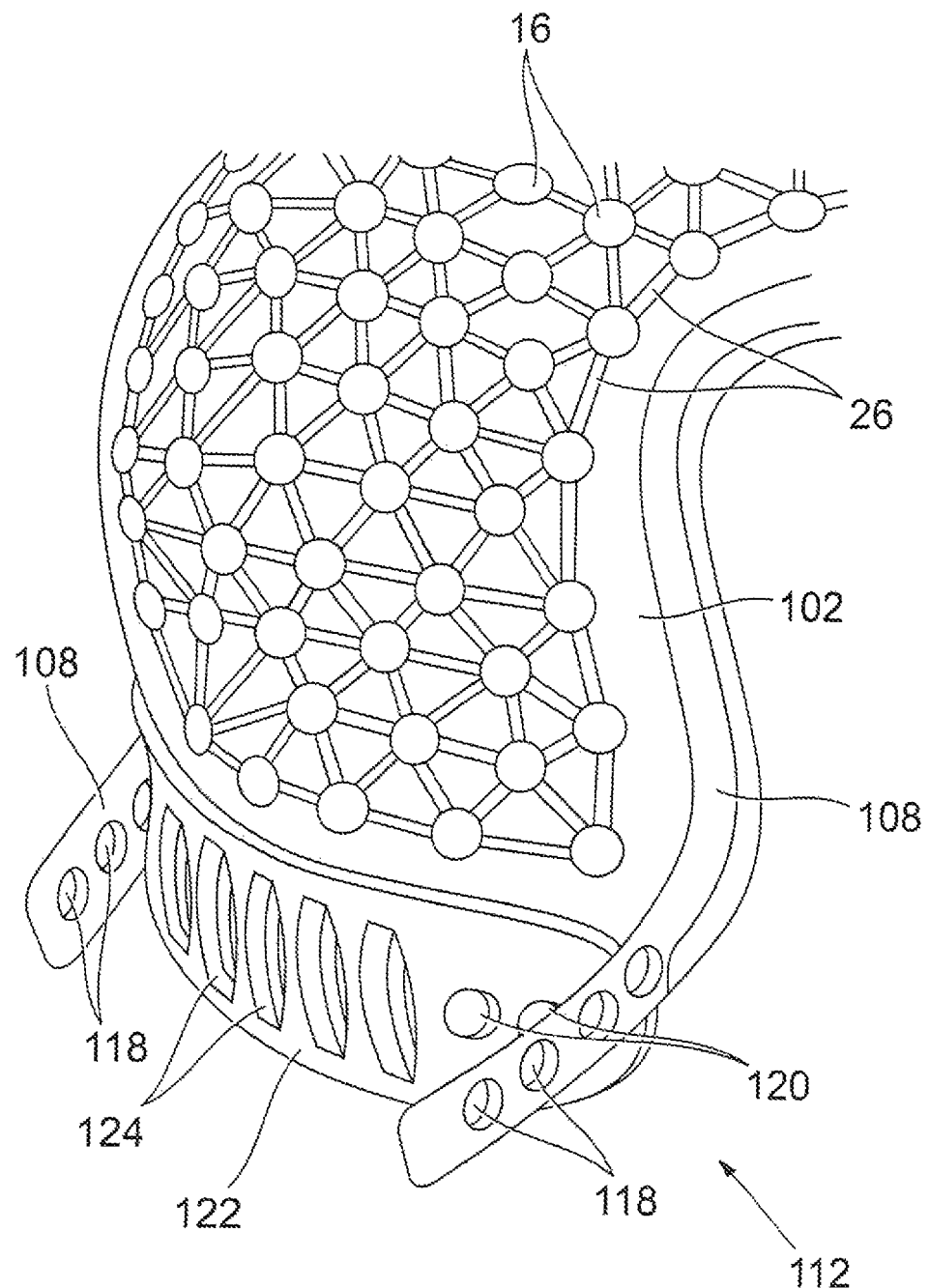
FIG. 6 is a partial side rear view of the wound dressing of FIG. 5.

Referring to FIG. 6, the rear adjusting means is a clip adjuster (112) of a kind similar to that known in the art. The clip adjuster (112) comprises a plurality of eyelets (118) positioned proximate a second end of each band member (108). The eyelets (118) are adapted to receive a corresponding projection (120) located on a mounting member (122). The number of eyelets (118) and corresponding projections (120) determine the number of adjustment positions that may be employed to increase the tension of a rearward section of the securing band (106). In the embodiment shown each band member (108) comprises four eyelets (118). As shown in FIG. 6, the mounting member (122) may incorporate a plurality of receiving loops (124) in which the ends of the band members (118) may be securely tucked away.

Each restraining member (114) is adapted to fit around an ear of a user. In the embodiment shown, a first end of the restraining member (114) is connected to the securing band (106) at a location proximate a front end of the wound dressing (100) and a second end is connected to securing band (106) proximate the rear end of the wound dressing (100).

The restraining members (114) act to restrict the removal of the headgear independently of the securing band (106) and together with the securing band (106) allow the wound dressing (100) to be secured on the head without the use of a chin strap or obscuring the ears.

While the frame structure of the wound dressing (100) has been described with particular reference to use in a headgear for use in reducing post-operative swelling of a head wound, or for controlling blood loss from head wounds, the unique frame structure described above may be incorporated in a headgear where securement of the headgear to the head of a user is required. For example the frame structure may be incorporated into a safety or protective helmet in order to provide a helmet without a chin strap.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:
1. A device comprising:
a sealed enclosure having at least one compartment;
a plurality of spaced apart pillars positioned within the at least one compartment;
a valve, wherein the valve is configured to evacuate air from the at least one compartment;
a connecting member connected to a first pillar and a second, neighboring, pillar of the plurality of spaced apart pillars; and
wherein the evacuation of air from the at least one compartment causes a reduction in a distance between at least two of the plurality of spaced apart pillars.

2. The device according to claim 1, wherein the plurality of spaced apart pillars are evenly spaced within the compartment.

3. The device according to claim 2, wherein the device is configured to serve as a wound dressing.

4. The device according to claim 1, wherein the plurality of spaced apart pillars are cylindrical columns.

5. The device according to claim 4, wherein the device is configured to serve as a wound dressing.

6. The device according to claim 1, wherein the connecting member defines a lattice-like structure.

7. The device according to claim 1, wherein the sealed enclosure comprises a first and second film layer.

8. The device according claim 7, wherein the first and second film layers are bonded together around their edges to define the sealed enclosure.

9. The device according to claim 7, wherein the plurality of spaced apart pillars are moveably retained between the first and second film layers.

10. The device according to claim 7, wherein the plurality of spaced apart pillars are retained in position between the first and second film layers by connection to the first and/or second film layer.

11. The device according to claim 7, wherein the plurality of spaced apart pillars are integrally formed with at least one of the first and second film layers.

12. The device according to claim 7, wherein a portion of the first film layer is adapted to be pulled into a space between the at least two spaced apart to reduce the distance between the at least two spaced apart pillars.

13. The device according to claim 1 further comprising a frame portion for attaching the wound dressing to a head of a patient.

14. The device according to claim 13, wherein the frame portion comprises a securing band for securing the wound dressing onto the head of the patient.

15. The device according to claim 14, wherein the frame portion comprises an adjuster, wherein the adjuster is configured to adjust a working length of the securing band.

16. The device according to claim 15, wherein the adjuster comprises a pawl and ratchet mechanism.

17. The device according to claim 15, wherein the adjuster comprises a clip adjuster.

18. The device according to claim 13, wherein the frame portion further comprises a restraining member.

19. The device according to claim 13, wherein the frame portion comprises a flexible plastic material.

20. The device according to claim 1, wherein the device is configured to serve as a wound dressing.

21. A method of reducing post-operative swelling of a body member of a human or animal patient, or for controlling blood loss from wounds, the method comprising:
  applying to the body member or wound a dressing formed by a sealed enclosure having at least one compartment and a plurality of spaced apart pillars;
  connecting, via a connecting member, a first pillar and a second, neighboring, pillar of the plurality of spaced apart pillars; and
  applying pressure onto the body member or wound by reducing a spacing between at least one pair of a plurality of spaced apart pillars by evacuating the at least one compartment of air.

22. The method as claimed in claim 21, wherein the dressing is a dressing according to claim 1.

* * * * *

UNITED STATES PATENT AND TRADEMARK OFFICE
CERTIFICATE OF CORRECTION

PATENT NO.        : 8,481,804 B2
APPLICATION NO.   : 12/999181
DATED             : July 9, 2013
INVENTOR(S)       : Jake Timothy Page 1 of 1

It is certified that error appears in the above-identified patent and that said Letters Patent is hereby corrected as shown below:

In the Claims:

Column 7, Line 29, Claim 12

Replace "at least two spaced apart to reduce"
With -- at least two spaced apart pillars to reduce --

Signed and Sealed this
Twenty-seventh Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,481,804 B2  Page 1 of 1
APPLICATION NO. : 12/999181
DATED : July 9, 2013
INVENTOR(S) : Jake Timothy It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 217 days.

Signed and Sealed this
Eighth Day of September, 2015

Michelle K. Lee
*Director of the United States Patent and Trademark Office*